United States Patent [19]

Blacklock et al.

[11] Patent Number: 5,189,177
[45] Date of Patent: Feb. 23, 1993

[54] CHIRAL BORON CATALYSTS FOR REDUCTION OF KETONES AND PROCESS FOR THEIR PREPARATION

[75] Inventors: Thomas J. Blacklock, Clark, N.J.; Todd K. Jones, Salan Beach, Calif.; David J. Mathre, Skillman; Lyndon C. Xavier, Edison, both of N.J.

[73] Assignee: Merck & Co., Inc., Rahway, N.J.

[21] Appl. No.: 730,316

[22] Filed: Jul. 15, 1991

Related U.S. Application Data

[63] Continuation-in-part of Ser. No. 510,768, Apr. 18, 1990, Pat. No. 5,039,802.

[51] Int. Cl.$^5$ ............................................. C07F 5/02
[52] U.S. Cl. ....................................... 548/405; 546/13
[58] Field of Search ........................................ 545/405

[56] References Cited

FOREIGN PATENT DOCUMENTS 237902 3/1987 European Pat. Off. .
305180 3/1989 European Pat. Off. .
3638M 5/1964 France .

OTHER PUBLICATIONS

Enders et al., *Org. Synth.*, Col. vol. 6, 642–549.
Corey et al., *J. Amer. Chem. Soc.*, 1987, 109, 7925–7926.
Kapfhammer et al., Hoppe-Seyler Zeit. Physiol Chem. 1933.233 43–52.
Corey et al., J. Org. Chem. 1988, 53, 2861–2863.
Corey et al., J. Amer. Chem. Soc. 1987 109, 5551–5553.
Enders et al., *Bull. Soc. Chem Belg.*, 1988, 97, 691–704.
Corey et al., Tet. Letters, 1989, 30 6375–6278.
Mathre et al. J. Org. Chem. 56, 751–762 (1991).

*Primary Examiner*—Mark L. Berch
*Attorney, Agent, or Firm*—William H. Nicholson; Joseph F. DiPrima

[57] ABSTRACT

The chiral catalyst of general structure 1, or its enantiomer

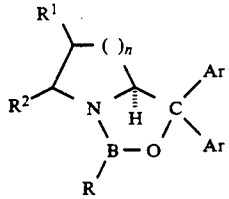

is prepared by treating the corresponding N-carboxy anhydride of structure 2

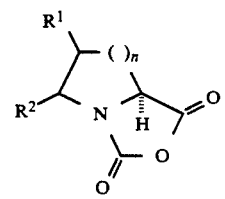

with an aryl metal, especially a phenyl metal such as an aryl magnesium halide, aryl lithium, aryl zinc or aryl cesium, to form a 1,1-diaryl- methanol of structure 3

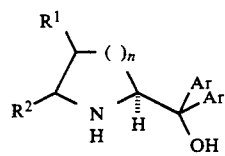

followed by treatment with a compound of structure, 4

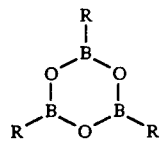

The catalyst, wherein R is aromatic, is novel and in some cases superior to the catalyst wherein R is alkyl or aralkyl in directing the chirality of diborane, borane-dimethyl sulfide or borane-tetrahydrofuran reductions of ketones to secondary alcohols.

11 Claims, No Drawings

CHIRAL BORON CATALYSTS FOR REDUCTION OF KETONES AND PROCESS FOR THEIR PREPARATION

RELATED APPLICATION

The present patent application is a continuation-in-part of our copending patent application Ser. No. 510,768 filed Apr. 18, 1990, now U.S. Pat. No. 5,039,802.

BACKGROUND OF THE INVENTION (S)-1,1-Diphenylprolinol the principal compound of structure 3 is a known compound and has been prepared by a variety of processes, all involving a fully protected pyrrolidine. See for example Enders et al., *Org. Synth.*, Col. Vol. 5, 542-549; Corey et al., *J. Amer. Chem. Soc.*, 1987, 109, 7925-7926; French Patent FR 3638M, 1965; Kapfhammer, et al. *Hoppe-Seylers Zeit. Physiol. Chem.* 1933, 223, 43-52; German Patent DE 3609152A1, 1987; Corey et al., *J. Amer. Chem. Soc.*, 1987, 109 5551-5553; *J. Org. Chem.* 1988, 53, 2861-2863; Enders et al., *Bull Soc. Chem. Belg.*, 1988, 97, 691-704. These prior art processes involve multiple steps and rather low overall yields.

For example preparation of (S)-1,1-diphenylprolinol via the procedure described in the literature [Corey et. al., *J. Am. Chem. Soc.* 1987, 109, 5551-5553] afforded a 30-40% overall yield of the amino-alcohol from (S)-proline. The process required multiple isolations [N-(benzyloxycarbonyl)(S)-proline (solid, commercially available), N-(benzyloxycarbonyl)-(S)-proline methyl ester (viscous oil), and (S)-1,1-diphenylprolinol hydrochloride (solid, precipitated from diethyl ether), and (S)-1,1-diphenylprolinol (solid recrystallized from water/methanol)]. The Grignard addition to N-benzyloxycarbonyl)-(S)-proline methyl ester required a large excess (8 equiv) of phenylmagnesium chloride. The initial addition to form the intermediate 1,1-diphenylprolinol oxazolidinone occurs quickly at 0° C. The addition of phenylmagnesium chloride to the oxazolidinone affording the desired product, however, is much slower-requiring 12-18 hours at room temperature. Isolation of the amino-alcohol from the large excess of magnesium salts also was a problem-requiring multiple extractions from a magnesium hydroxide gel. The resultant product had an enantiomeric purity of 99:1 (S:R) by capillary GC (DB-23) of the Mosher amide derivative.

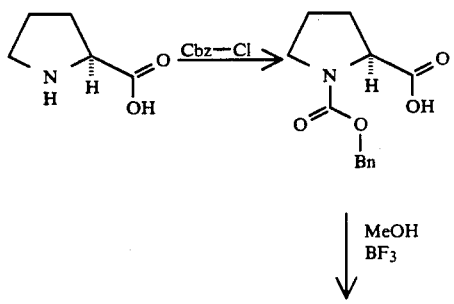

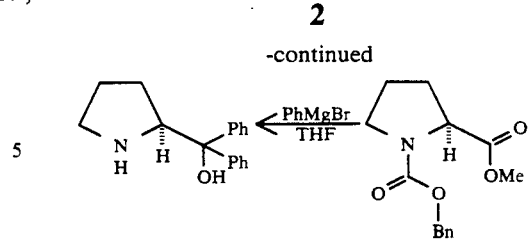

The methods reported for preparation of structure 1 (n=1, Ar=Rh, R=Me, R¹,R²=H), include reaction of the corresponding prolinol with methylboronic acid (1.1 equiv.) in toluene at 1) 23° C. in the presence of 4 Å molecular sieves for 1.5 hours or 2) at reflux for 3 hours using a Dean-Stark trap for water removal; both followed by evaporation of solvent, and molecular distillation (0.1 mm, 170° C.) (Corey et al., *J. Amer. Chem Soc.*, 1987, 109, 7925-7926). An alternate method reported for preparation of structure 1 (n=1, Ar=2-naphthyl, R=Me, R¹R²=H) involved heating a toluene solution of the corresponding prolinol and methylboronic acid (1.2 equiv) at reflux for 10 hours using a Soxhlet extractor containing 4 Å molecular sieves (Corey et al., *Tetrahedron Lett.*, 1989, 30, 6275-6278). The key to these procedures is irreversible removal of two molecules of water, thus driving the reaction to completion. Chiral reductions using oxazaborolidine prpared via these methods provided erratic results with respect to yields and enantiomeric purity of the reduction products.

Now, with the present invention there is provided a novel improved procedure for preparation of the diarylmethanol 3; a novel improved method for the preparation of the oxazaborolidine catalyst, 1; and novel improved catalysts.

SUMMARY OF THE INVENTION

This invention is concerned with a novel process for preparing a diarylmethanol 3 especially a 1,1-diarylprolinol, which comprises treating the corresponding N-carboxy anhydride 2 with an aryl metal, especially a phenyl metal, such as an aryl lithium, aryl zinc, aryl cesium or aryl magnesium halide, especially the chloride:

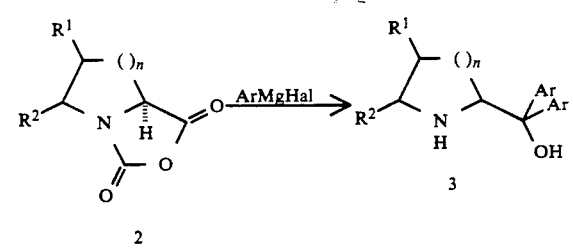

The invention is also concerned with a process for preparing a chiral catalyst 1 by treating the 1,1-diarylmethanol with a trisubstituted boroxine 4;

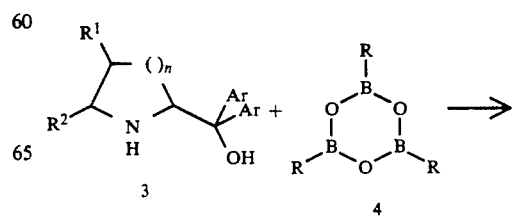

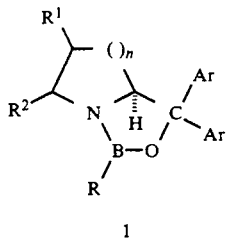

The invention is also concerned with the novel catalyst 1, wherein R is an aromatic group, either unsubstituted or substituted.

The catalyst produced by the novel process of this invention is useful for directing the chirality of reductions of ketones with boranes such as diborane, borane-dimethyl sulfide, or borane-THF to chiral secondary alcohols such as in the synthesis of a chiral intermediate 5 in the synthesis of the known carbonic anhydrase inhibitor 6 useful in the treatment of ocular hypertension and glaucoma.

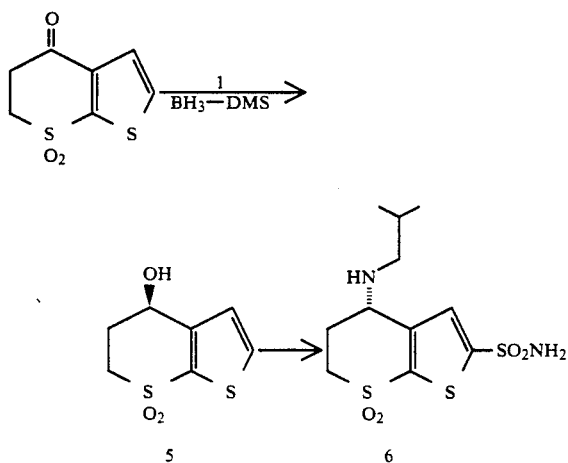

DETAILED DESCRIPTION OF THE INVENTION

The novel process for preparation of the diarylmethanol 3 comprises reacting an N-carboxyanhydride 2 with an aryl Grignard reagent:

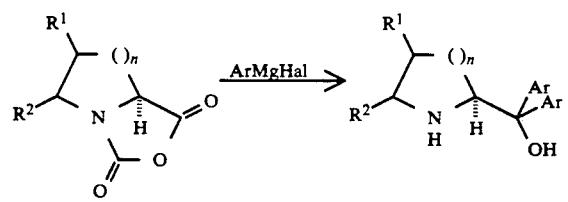

wherein n is 1 or 2; $R^1$ and $R^2$ independently represent hydrogen, $C_{1-3}$alkyl or joined together represent with the carbons to which they are attached a benzo group or a double bond; Ar is (1) 2-naphthyl, (2) phenyl, or (3) phenyl substituted in the meta-and or para- positions with one or more of (i) halo, such as fluoro or chloro, (ii) $C_{1-4}$alkyl, (iii) $CF_3$ or (iv) $C_{1-4}$alkoxy.

The N-carboxyanhydride, 2, is synthesized from the corresponding amino acid such as (S)-proline in <95% yield by reaction with phosgene, diphosgene or triphosgene in THF followed by addition of triethylamine and filtration to remove the resultant triethylamine hydrochloride as described by Fuller et al., *Biopolymers,* 1976, 15, 1869–1871.

The novel process for converting the N-carboxyanhydride, 2, to the diarylmethanol, 3, comprises reacting an ArMgHal preferably ArMgCl, Girgnard reagent with the N-carboxyanhydride in an ethereal solvent such as THF, diethyl ether or 1,2-dimethoxyethane, preferably THF at about −26° to 10° C. over a period of about 2 to 5 hours. It is preferred to add the N-carboxyanhydride to the Grignard reagent slowly (about 1 L/hour) to provide maximum yield and minimum racemization.

The diarylmethanol is isolated by slowly quenching the reaction with aqueous acid, preferably dilute sulfuric acid at about 0°–20° C., filtration to remove sulfate salts, concentration to a small volume and filtration to collect the sulfate salt of the diaryl methanol product 3 which can be further purified by washing with water and ethyl acetate and dried.

The novel process of this invention for preparation of the B-methyl oxazaborolidine catalyst (precursor) comprises reacting the diarylmethanol with a trimethylboroxine:

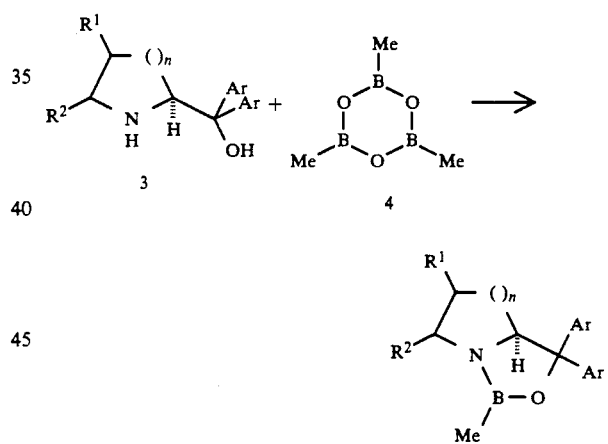

The process for the preparation of B-methyloxazaborolidines comprises the reaction of trimethylboroxine (0.67 to 1.0 equiv) with the diarylmethanol in an organic solvent such as toluene, benzene, xylene, chlorobenzene or the like at about 0° C. to 30° C. for about 0.5 to 4 hours until formation of the intermediate 7 is complete. The solvent is partially evaporated followed by multiple additions/concentrations of toluene or benzene to ensure complete removal of water and the methylboronic acid by product.

The novel intermediate of this invention has the structural formula 7; wherein n, Ar, $R^1$ and $R^2$ are as previously defined. It is preferred that n be 1, $R^1$ and $R^2$ be hydrogen, and that Ar be phenyl.

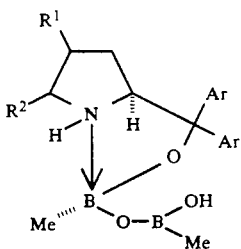

7

Another aspect of the present invention is the preparation of compounds of the formulas

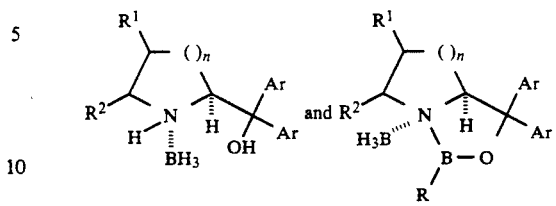

Specific instances of these compounds are illustrated in examples 12 and 33, respectively. These compounds are prepared by dissolving their amine or oxazaborolidine precursors of the respective following formulas

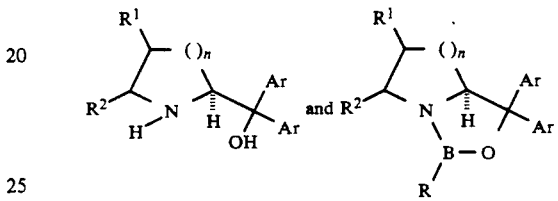

The novel process of this invention for preparation of the B-$C_{1-4}$alkyl oxazaborolidine or B-aryl oxazaborolidine catalyst (precursor) comprises reacting the diaryl methanol with a boroxine:

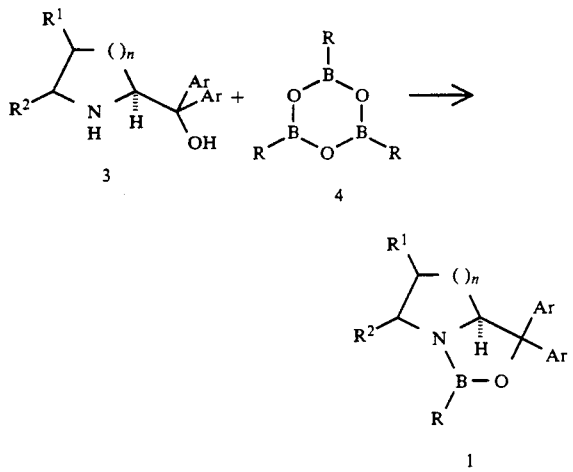

in a suitable solvent such as, for example benzene, toluene, xylene and chlorobenzene, and adding a source of $BH_3$ such as, for example diborane, and borane-dimethylsulfide, followed by recovery of the desired product, for instance by crystallization.

EXAMPLES

General

Melting points were determined on a Haake-Buchler melting point apparatus and are uncorrected. IR spectra were recorded on a Perkin-Elmer 1420 (as solutions in $CCl_4$) or a Nicolet 60SX FTIR spectrometer on microcrystalline solids using a Spectrascope accessory run at 4 $cm^{-1}$ resolution. NMR spectra were recorded in deuterochloroform or deuteroacetonitrile on a Bruker AM-250 ($^1H$, $^{13}C$), WM-250 ($^1H$, $^{11}B$, $^{13}C$), or AM-400 ($^1H$, $^{11}B$, $^{13}C$) spectrometer. $^1H$ chemical shifts are reported in ppm from an internal standard of residual chloroform (7.27 ppm) or acetonitrile (1.93 ppm). $^{11}B$ chemical shifts are reported in ppm from an external reference of boron trifluoride etherate (0.0 ppm). $^{13}C$ chemical shifts are reported in ppm from the central peak of deuterochloroform (77.0 ppm) or deuteroacetonitrile (1.3 ppm). Specific rotations were determined on a Perkin-Elmer 241 polarimeter. Concentrations (c) for specific rotations are reported in units of g/100 mL. Analytical gas chromatography (GC) was carried out on a Hewlett-Packard 5890A gas chromatograph equipped with a 7673A auto-sampler, split-mode injector, and flame-ionization detector, with helium as the carrier gas. The following capillary columns were employed: 30 m×0.32 mm DB-1 (J&W Associates) and 30 m×0.32 mm DB-23 (J&W Associates). Analytical high-performance liquid chromatography (HPLC) was carried out on a Hewlett-Packard Modular 1050 HPLC (quaternary pump and programmable variable-wavelength detector) using Column A: 250×0.46 mm DuPont Zorbax RX or Column B: 250×0.46 mm E. Merck Chirasphere. Analytical thin layer chromatography (TLC) was carried out on EM 0.25 mm silica gel 60 F HPTLC plates using the followwherein R is (1) $C_{1-4}$alkyl, preferably methyl, butyl, (2) phenyl, (3) phenyl substituted with one or more of (i) halo, such as fluoro or chloro, (ii) $C_{1-4}$alkyl, (iii) $CF_3$, or (iv) $C_{1-4}$alkoxy.

The process comprises the reaction of a boroxine (0.33 equiv) with the diarylmethanol in an organic solvent such as toluene, benzene, xylene, chlorobenzene or the like at about 0° C. to 30° C. for about 0.5 to 4 hours, then at 80° C. to 150° C. for about 12 to 24 hours with concurrent removal of water, using a Dean-Stark trap, molecular sieves, or azeotropic distillation.

The novel catalyst of this invention has structural formula 1;

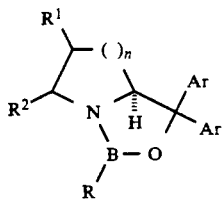

wherein n, Ar, $R^1$ and $R^2$ are as previously defined and R is (1) phenyl, (2) phenyl substituted with one or more of (i) halo, such as fluoro or chloro, (ii) $C_{1-4}$alkyl, (iii) $CF_3$, or (iv) $C_{1-4}$alkoxy.

It is preferred that n be 1, $R^1$ and $R^2$ be hydrogen, and that Ar be phenyl. It is also preferred that R be phenyl substituted with 4-fluoro or 4-$C_{1-4}$alkyl group, especially methyl.

ing solvent systems: solvent A (45:45:9:1 hexane/dichloromethane/isopropanol/28% aq NH$_4$OH; solvent B (7:3 hexane/EtOAc). Visualization was accomplished with UV light and/or by spraying with aqueous cerric ammonium molybdate followed by heating. Mass spectra were obtained on a Finnigan-MAT TSQ 70 B Mass Spectrometer using either GC/MS with chemical ionization (NH$_3$) or FAB/MS using a DTT/DTE matrix. Combustion analyses were obtained in-house from our Analytical Research Department.

Reactions were carried out under an atmosphere of dry N$_2$. As necessary Et$_3$N, THF and toluene were dried over 3 Å or 4 Å molecular sieves. Residual water content was determined by Karl Fisher (KF) titration. (S)-Proline was obtained from Ajinomoto, (R)-proline from Tanabe USA, Inc. Phosgene (1.93M in toluene) was obtained from Fluka. Phenylmagnesium chloride (2M in THF) was obtained from Boulder Scientific. Other Grignard reagents were either obtained from Aldrich, or prepared from the corresponding aryl bromide. Trimethylboroxine and n-butylboronic acid were obtained from Aldrich. Triarylboroxines were prepared from the corresponding arylboronic acids by heating a toluene solution at reflux for 3–4 hours using a Dean-Stark trap for water removal, followed by evaporation of the solvent. (R)-MTPA (Aldrich) was converted to the acid chloride using oxalyl chloride (1.2 equiv) and catalytic DMF (0.05 equiv) in dichloromethane at 20°–25° C. for 4 hours followed by Kugelrohr distillation (45° C., 0.1 mBar).

The following examples illustrate the present invention without, however, limiting the same thereto.

EXAMPLE 1

Step A: Preparation of (S)-Tetrahydro[1H,3H]pyrrolo[1,2-c]oxazole-1,3-dione

A 5-L, three necked flask fitted with a mechanical stirrer, nitrogen inlet tube, 1-L addition funnel, and teflon coated thermocouple probe containing dry THF (1.15 L), was charged with (S)-proline (115 g, 1.00 mol). To the well-stirred, cooled (15°–20° C.) suspension was added a solution of phosgene in toluene (1.93M, 622 mL, 1.20 mol) over a 0.5–1.0 hour period, maintaining the internal temperature at 15°–20° C. Caution: phosgene is an insidious poison. All manipulations with phosgene should be performed in a hood with good ventilation. Any excess phosgene should be decomposed in cold aqueous base. After the phosgene addition was complete, the mixture was warmed to 30°–40° C. and aged for 0.5 hour. During this time the mixture became homogeneous as proline reacted with phosgene to afford the intermediate N-carbamoyl chloride. Once homogeneous, the reaction mixture was aged an additional 0.5 hour at 30°–35° C., then cooled to 15°–20° C. While maintaining the internal temperature at 15°–20° C., the reaction mixture was concentrated in vacuo (1000 down to 50 mBar) to a volume of about 150 mL. Caution: hydrogen chloride (1 mol) and excess phosgene (200 mmol) are removed during the distillation. The use of appropriate traps, and venting of the vacuum pump to the hood is required. The reaction can be assayed at this point by $^1$H NMR: (about 30 μL dissolved in 0.6 mL CDCl$_3$) δ11.5–10.0 (br s, 1H, CO$_2$H), 7.3–7.1 (m, toluene), 4.62 (dd, 0.4H, C2-H rotamer), 4.50 (dd, 0.6H, C2-H rotamer), 3.9–3.5 (m, 2H, C5-H$_2$), 2.5–1.8 (m, 4H, C3-H$_2$, C4-H$_2$). [The spectrum should not contain resonances at δ4.9 (dd, 0.4H, C2-H rotamer) and 4.7 (dd, 0.6H, C2-H rotamer) corresponding to proline N-carbamoyl chloride, acid chloride.] The residue was dissolved in dry THF (1.15 L), and the solution cooled to 0°–5° C. With good agitation, dry Et$_3$N (106 g, 1.05 mol) was added over 15 minute while maintaining the internal temperature at 0°–5° C. After the addition was complete, the mixture was aged for 0.5 hour at 0°–5° C., then filtered through an enclosed, medium frit, sintered glass funnel. The resultant cake of Et$_3$N•HCl was washed with THF (3×200 mL). The filtrate and THF washes were combined to afford a solution containing product (about 0.95–1.0 mol) in THF (about 1.75 L) that was used immediately "as is" without further purification.

For analysis, a portion of the THF solution was concentrated in vacuo (20° C., 50 mBar) and the resultant white solid dried in vacuo (20° C., 0.01 mBar) overnight: mp 51°–52° C.; IR (CCl$_4$): 2980, 1845, 1780, 1350, 950, 920 cm$^{-1}$; $^1$H NMR (CDCl$_3$) δ4.34 (dd, J=7.4, 8.7 Hz, 1H, C2-H), 3.72–3.68 (m, 1H, C5-H$_2$), 3.32–3.18 (m, 1H, C5-H$_2$), 2.4–1.8 (m, 4H, C3-H$_2$, C4-H$_2$); $^{13}$C NMR (CDCl$_3$) δ168.9 (C3), 154.9 (C1), 63.1 (C3a), 46.5 (C6), 27.6 (C4), 26.9 (C5).

Anal. Calcd for C$_6$H$_7$NO$_3$: C, 51.06; H, 4.96; N, 9.93. Found: C, 51.23; H, 4.84; N, 9.65.

Step B: Preparation of (S)-α,α-Diphenyl-2-pyrrolidinemethanol

A 5-L three-necked flask fitted with a mechanical stirrer, nitrogen inlet tube, 2-L addition funnel containing the THF solution of product from Step A, and teflon coated thermocouple probe, was charged with a solution of phenyl magnesium chloride in THF (2.0M, 1.5 L, 3.0 mol). The Grignard reagent was cooled to −15° C. The THF solution of product from Step A (about 0.95–1.0 mol) was added over a 1 hour period while maintaining the internal temperature at −10° to −15° C. After the addition was complete, the mixture was aged for 3 hours at −15° C. and 1 hour at 0° C. The reaction was quenched into a 12-L mechanically stirred flask, containing a pre-cooled (0° C.) solution of 2M aqueous H$_2$SO$_4$ (2.0 L, 4.0 mol), over a 0.5–1.0 hour period while maintaining the internal temperature below 20° C. During the quench, a thick white precipitate of MgSO$_4$ formed. The mixture was agitated for 1 hour at 0° C., and filtered through a 3-L, medium frit, sintered glass funnel. The MgSO$_4$ cake was washed free of residual product with THF (3×1.0 L). The filtrate and THF washes were combined and concentrated at atmospheric pressure to a volume of 2.0 L. Caution: benzene (about 82 g), formed during the quench of excess PhMgCl, is removed during the concentration. The product, as its sulfate salt, Ph$_2$CO, and Ph$_3$COH precipitate during the concentration. The mixture was cooled to 0°–5° C., aged 1 hour, and filtered. The cake was washed with H$_2$O (2×200 mL) to remove excess H$_2$SO$_4$, and EtOAc (3×350 mL) to remove the Ph$_2$CO and Ph$_3$COH. The cake was dried in vacuo (40° C., 50 mBar) affording 221 g (73% from proline) of the sulfate salt of the product as a white solid: mp 275°–290° C. (dec).

Anal. Calcd for C$_{34}$H$_{40}$N$_2$O$_6$S: C, 67.52; H, 6.67; N, 4.63. Found: C, 67.75; H, 6.67; N, 4.51.

A portion of the sulfate salt was converted to the free base as follows: to a mechanically stirred solution of THF (50 mL) and 2M aqueous NaOH (50 mL, 100 mmol) at 20° C. was added the sulfate salt (15.1 g, 50.0 mmol). The mixture was stirred at 20° C. until all solids dissolved, and was then diluted with toluene (200 mL). The two-phase mixture was filtered through a medium frit sintered-glass funnel, partitioned, and the organic layer washed with H₂O (25 mL). The organic layer was concentrated in vacuo (50° C., 1 mBar) affording 12.5 g (99% yield) of product as a colorless oil that crystallized on standing. An analytical sample was prepared by recrystallization from hexane: mp 79°-79.5° C. [Lit. mp

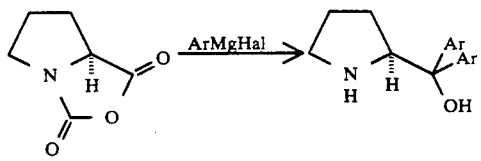

TABLE I

| Example | Ar | Yield | m.p. (°C.) | $[\alpha]_{589}^{22}$ |
|---|---|---|---|---|
| 2 | 4-F—C₆H₄— | 90 | 89.5-90 | −48.5° (c = 0.323, MeOH) |
| 3 | 4-Cl—C₆H₄— | 59 | 114.5-115 | −37.7° (c = 0.339, MeOH) |
| 4 | 4-CH₃—C₆H₄— | 57 | 94-94.5 | −43.4° (c = 0.305, MeOH) |
| 5 | 4-CF₃—C₆H₄—[1] | 46 | 280-300[2] | −34.2° (c = 0.789, MeOH) |
| 6 | 4-t-Bu-C₆H₄— | 50 | 165.7-166.1 | −25.1° (c = 0.389, MeOH) |
| 7 | 4-CH₃O—C₆H₄—[3] | 53 | — | −44.1° (c = 0.607, MeOH) |
| 8 | 3-Cl—C₆H₄— | 62 | — | −49.1° (c = 0.804, MeOH) |
| 9 | 3,5-Cl₂—C₆H₃— | 68 | 118-119 | −36.6° (c = 1.409, MeOH) |
| 10 | 3,5-(CH₃)₂—C₆H₃— | 60 | 97.5-98.0 | −63.0° (c = 0.318, MeOH) |
| 11 | 2-naphthyl | 64 | 142.5-143.5 | −99.1° (c = 0.702, MeOH) |

[1] Product is an oil. It was purified by conversion to its HCl salt, recrystallization, and conversion to free base. Yield and rotation are of the purified oily product.
[2] Melting point of the HCl salt.
[3] Product is an oil. It was purified by liquid chromatography on silica gel. Yield and rotation are of the purified oily product.

76.5°-77.5° C. (H₂O/MeOH); mp 80°-82° C. (EtOH)]; IR (CCl₄) 3600-3300 (br), 3170, 3140, 2980, 2790, 1490, 1450, 1400, 1170 cm⁻¹; ¹H NMR (CDCl₃) δ7.7-7.5 (m, 4H, Ar-H), 7.4-7.1 (m, 6H, Ar-H), 4.65 (s, 1H, O—H), 4.3 (t, J=7.4 Hz, 1H, C2-H), 3.1-2.9 (m, 2H, C5-H₂), 1.9-1.5 (m, 5H, C3-H₂, C4-H₂, N—H); ¹³C NMR (CDCl₃) δ148.21, 145.41 (C1', C1''), 128.24, 127.98 (C3', C3'', C5', C5''), 126.46, 126.36 (C4', C4''), 125.88, 125.55 (C2', C2'', C6', C6''), 77.1 (Cα), 64.41 (C2), 46.68 (C5), 26.30 (C3), 25.51 (C4); GC/MS: [M+H]⁺ at m/z 254.1; TLC (solvent A) R$_f$= 0.32; $[\alpha]_{589}^{21}$ −54.3° (c=0.261, MeOH) [Lit. $[\alpha]_{58}^{24}$ −58.8° (c=3.0, MeOH)].

Anal. Calcd for C₁₇H₁₉NO: C, 80.60; H, 7.50; N, 5.53. Found: C, 80.80; H, 7.64; N, 5.49.

Chiral Assay: To a magnetically stirred suspension of Step B product (sulfate salt) (30 mg, 100 μmol) in THF (1 mL) was added 1.0M aq NaOH (210 μL, 210 μmol). The mixture was stirred until all of the solid dissolved (about 15 minute), then (R)-MTPA acid chloride (27 mg, 107 μmol) was added, and the mixture stirred for 1 hour at 20° C. The reaction can be monitored by TLC (solvent B) Step B product (R$_f$=0.05), (R,R)-derivative (R$_f$=0.78), (R,S)-derivative (R$_f$=0.71). After completion, the mixture was diluted into hexane (9 mL), centrifuged, and the upper, organic layer eluted through a Baker silica SPE (1 g) column (previously washed with hexane). The column was eluted with additional 8:2 (v/v) hexane/THF (5 mL). The combined eluate was analyzed by either GC (DB-23, 250° C.) to detect 0.3% of the (R,R)-derivative (19.1 minute) and 99.7% of the (R,S)-derivative (20.7 minute); or HPLC (Zorbax Si, 9:1 hexane/THF, 210 nm) to detect 0.3% of the (R,R)-derivative (k'=1.21) and 99.7% of the (R,S)-derivative (k'=1.66).

Employing the procedure substantially as described in Example 1, Step B, but substituting for the phenylmagnesium chloride used therein an equimolecular amount of the Grignard reagents depicted in Table I, there are produced the diarylmethanols also described in Table I.

EXAMPLE 12

Preparation of (S)-α,α-Diphenyl-2-pyrrolidinemethanol-borane complex

A 250-mL three-necked flask fitted with a mechanical stirrer, nitrogen inlet tube, and teflon coated thermocouple probe, was charged with a solution of the free base product of Example 1 Step B (20.7 g, 81.7 mmol) in dry toluene (100 mL). To the stirred solution at 20° C. was added borane-dimethyl sulfide (10M, 10.0 mL, 100 mmol) over 5 minutes via syringe. The borane reacted immediately in an exothermic reaction (raising the internal temperature from 20° C. to 32° C.) forming a thick white precipitate. With continued stirring, the mixture was allowed to cool to room temperature (20° C.) over a 1 hour period. The mixture was filtered, and the product cake washed with dry toluene (25 mL). The product was dried in vacuo (20° C., 0.01 mBar) to constant weight. Yield 15.7 g (72%) of a white crystal line solid. m.p. 130°-132° C. (dec). ¹H NMR (CDCl₃) δ7.7-7.1 (m, 10H, Ar-H), 5.15 (s, 1H, —OH), 4.5 (br, 1H, —NH), 4.2 (m, 1H, C2-H), 3.25 (m, 2H, C5-H₂), 2.6 (m, 1H, C4-H), 2.3 (m, 1H, C4-H), 1.85 (m, 1H, C3-H), 1.6 (m, 1H, C3-H), 2.1-0.7 (br, 3H, BH₃). ¹³C NMR (CDCl₃) δ145.8, 144.5 (C1', C1''), 129.1, 128.2 (C3', C5', C3'', C5''), 127.4, 127.0 (C4', C4''), 125.2, 125.1 (C2', C6', C2'', C6''), 76.5 (Cα), 69.6 (C2), 55.6 (C5), 20.6 (C4), 19.9 (C3).

Anal. Calcd for C₁₇H₂₂BNO: C, 76.46; H, 8.24; N, 5.25.

Found: C, 76.54; H, 8.16; N, 5.18.

EXAMPLE 13

Preparation of (S)-Tetrahydro-1-methyl-3,3-diphenyl-1H,3H-pyrrolo[1,2-c][1,3,2]oxazaborole A 3-L, three necked flask fitted with a mechanical stirrer, nitrogen inlet tube, and teflon coated thermocouple, was charged with the sulfate salt of the product of Example 1, Step B (89.1 g, 295 mmol), THF (300 mL), and 2M aqueous NaOH (300 mL). The mixture was stirred at 20°-25° C. until all of the solid dissolved (about 0.5 hour). Toluene (1.2 L) was added, the mixture stirred an additional 0.5 hour, filtered through a medium frit sintered glass funnel, and partitioned. The upper (product) layer was washed with water (150 mL) and concentrated (1 atm) to a volume of about 500 mL. The toluene solution was cooled to 20°-25° C. and charged with trimethylboroxine (24.7 g, 197 mmol). The temperature of the mixture rose about 5° C., and a white precipitate of intermediate 7 formed. The mixture was aged 0.5 hour at 20°-25° C., then toluene (500 mL) was added, and the mixture concentrated (1 atm) to a volume of about 300 mL. The toluene addition, followed by concentration, was repeated two times to insure complete removal of water and excess methylboronic acid (as trimethylboroxine). The suitability of the catalyst was determined by both capillary GC: (DB-1, 200° C.) <1% starting material (5.5 minute), >99% product (4.9 minute), and $^1$H NMR: (CDCl$_3$) no starting material δ4.3 (t), trimethylboroxine δ0.45 (s), intermediate 5 δ0.35 to −0.50 (multiple B-CH$_3$ singlets), and/or water addition product δ−0.25 (br, B-CH$_3$). The toluene solution of oxazaborolidine (about 1.0M), stored under an atmosphere of N$_2$ protected from moisture, was used "as is" as a catalyst for the enantioselective reduction of ketones with borane.

For analysis, a portion of the toluene solution (10.0 mL) was concentrated in vacuo (50° C., 0.001 mBar) to afford 2.77 g of product as a white solid: mp 79°-81° C. [Lit. mp 74°-87° C.]; IR (CCl$_4$) 2960, 2880, 1440, 1330, 1310, 1235, 1000 cm$^{-1}$; $^1$H NMR (0.2M in CDCl$_3$) δ7.65-7.15 (m, 10H, Ar-H), 4.4 (dd, J=5.8, 10.0 Hz, 1H, C3a-H), 3.45-3.30 (m, 1H, C6-H), 3.15-3.00 (m, 1H, C6-H), 1.90-1.55 (m, 3H, C4-H, C5-H$_2$), 0.95-0.75 (m, 1H, C4-H), 0.40 (s, 3H, BCH$_3$); $^{11}$B NMR (0.2M in CDCl$_3$) δ34.3; $^{13}$C NMR (0.2M in CDCl$_3$) δ147.6, 144.0 (C1', C1''), 128.2, 127.7 (C3', C3'', C5', C5''), 127.1, 126.6 (C4', C4''), 126.3, 126.2 (C2', C2'', C6', C6''), 87.8 (C3), 72.7 (C3a), 42.9 (C6), 30.2 (C4), 26.4 (C5), −5.6 (br, B-CH$_3$). FAB/MS (DTT/DTE matrix): [M+H]$^+$ at m/z 278.1. Isotopic cluster consistent with the presence of one boron.

Anal. Calcd for C$_{18}$H$_{20}$BNO: C, 78.00; H, 7.27; N, 5.05.

Found: C, 77.81; H, 7.37; N, 4.91.

EXAMPLE 14

Preparation of Intermediate 7

To a magnetically stirred solution of the free base product of Example 1, Step B (5.06 g, 20.0 mmol) in dry toluene (20 mL) at 20° C. was added trimethylboroxine (1.67 g, 13.3 mmol). The reaction was exothermic, raising the temperature to 33° C. The solution was allowed to cool to 20° C., then aged at that temperature for 1 hour. The resultant solid was isolated by filtration. The solid was dried in vacuo (45° C., 0.1 mBar) to afford 6.07 g (90%) of intermediate 7. An analytical sample was prepared by recrystallization from EtOAc: mp 147°-148° C.; IR (solid) 3435, 3270, 3066-2885, 1596, 1492, 1447, 1484, 1302, 1247, 1141, 1046, 1030, 1015, 1006, 762, 752, 717, 701; $^1$H NMR (CD$_3$CN, major diasteromer) δ7.66 (m, 2H, o-Ar-H), 7.47 (m, 2H, o-Ar-H), 7.3-7.1 (overlapping m, 6H, Ar-H), 6.37 (s, 1H, B-OH), 5.13 (br, 1H, NH), 4.68 (dt, J=11.1, 6.5, 1H, C3a-H), 3.39 (m, 1H, C6-H), 2.99 (m, 1H, C6-H), 1.9-1.7 (overlapping m, 3H, C5-H$_2$, C4-H), 1.44 (m, 1H, C4-H), 0.09 (s, 3H, —OB(OH)CH$_3$), −0.49 (s, 3H, B1-CH$_3$); $^{11}$B NMR (CDCl$_3$, major diasteromer) δ30.4 (—OB-(OH)CH$_3$), 7.8 (B1); $^{13}$C NMR (CD$_3$CN, major diasteromer) δ148.4, 147.9 (C1', C1''), 129.0, 128.8 (C3', C5', C3'', C5''), 127.7, 127.2 (C4', C4''), 126.8, 126.1 (C2', C6', C2'', C6''), 83.6 (C3), 68.6 (C3a) 45.6 (C6), 28.7 (C4), 24.6 (C5), 7.0 (v br, B1-CH$_3$), −0.2 (v br, —OB(OH)C$_3$). FAB/MS (DTT/DTE matrix): [M+H]$^+$ at m/z 338.2. Isotopic cluster consistent with the presence of two borons.

Anal. Calcd for C$_{19}$H$_{25}$B$_2$NO$_3$: C, 67.71; H, 7.48; N, 4.16.

Found: C, 67.59; H, 7.47; N, 4.15.

Employing the procedure substantially as described in Example 13, but substituting for the diphenylmethanol used therein, comparable amounts of the diarylmethanols described in Table II, there were produced the B-methyl oxazaborolidines also described in Table II:

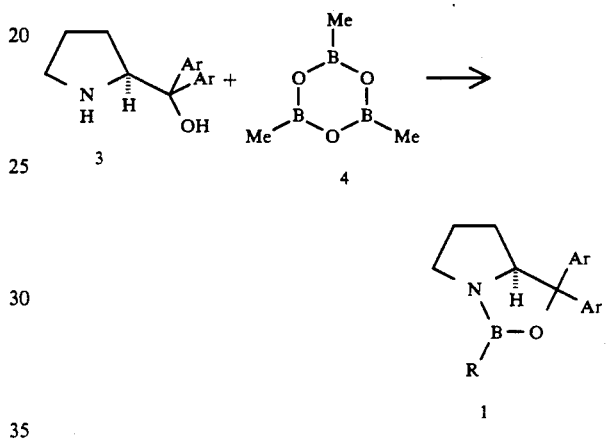

TABLE II

| Example | Ar | Purity (%) |
|---|---|---|
| 15 | 4-F—C$_6$H$_4$—[1] | 98 |
| 16 | 4-Cl—C$_6$H$_4$—[1] | 99 |
| 17 | 4-CH$_3$—C$_6$H$_4$— | 99 |
| 18 | 4-CF$_3$—C$_6$H$_4$—[1] | 99 |
| 19 | 4-t-Bu-C$_6$H$_4$— | 99 |
| 20 | 4-CH$_3$O—C$_6$H$_4$— | 99 |
| 21 | 3-Cl—C$_6$H$_4$— | 99 |
| 22 | 3,5-Cl$_2$—C$_6$H$_3$— | 99 |
| 23 | 3,5-(CH$_3$)$_2$—C$_6$H$_3$— | 99 |
| 24 | 2-naphthyl | 99 |

[1]Reaction run in benzene.

EXAMPLE 25

Preparation of (S)-Tetrahydro-1-n-butyl-3,3-diphenyl-1H,3H-pyrrolo[1,2-c][1.3.2]oxazaborole A solution of the free base product from Example 1, Step B (20.1 g, 79.4 mmol) and tri-n-butylboroxine (6.66 g, 26.5 mmol) in toluene (200 mL) was aged 0.5 hour at 20°-25° C., then heated at reflux for 16 hours using a Dean-Stark trap for water removal. The solution was concentrated (1 atm) to a volume of about 70 mL. The suitability of the catalyst was determined by both capillary GC: (DB-1, 200° C.) <0.1% tri-n-butylboroxine (1.3 minute), <1% starting material (5.7 minute), >98% product (9.7 minute), and $^1$H NMR: (CDCl$_3$) no starting material δ4.25 (t). Based on the final volume of 70 mL, the concentration of the oxazaborolidine was calculated to be 1.13M. The toluene solution, stored under an atmosphere of N$_2$ protected from moisture, was used "as is" as a catalyst for the enantioselective reduction of ketones with borane.

For analysis, a portion of the toluene solution (5.00 mL) was concentrated in vacuo (50° C., 0.001 mBar) to afford 1.80 g of the product as a colorless oil: IR (CCl$_4$) 3060, 3020, 2960, 2930, 2880, 1480, 1440, 1240, 1000 cm$^{-1}$; $^1$H NMR (0.2M in CDCl$_3$) δ7.65-7.45 (m, 2H, Ar-H), 7.45-7.05 (m, 8H, Ar-H), 4.35 (dd, J=5.6, 9.9 Hz, 1H, C3-H), 3.45-3.30 (m, 1H, C6-H), 3.15-3.00 (m, 1H, C6-H), 1.90-1.25 (m, 7H, C4-H, C5-H$_2$, C2'-H$_2$, C3'-H$_2$), 1.05-1.70 (m, 6H, C4-H, C1'-H$_2$, C4'-H$_3$); $^{11}$B NMR (CDCl$_3$) δ34.3; $^{13}$C NMR (0.2M in CDCl$_3$) δ147.8, 144.1 (C1'', C1'''), 128.1, 127.7 (C3'', C3''', C5'', C5'''), 127.1, 126.5 (C4'', C4'''), 126.22, 126.16 (C2'', C2''', C6'', C6'''), 87.4 (C3), 73.1 (C3a), 42.8 (C6), 30.2 (C4), 26.9 (C2'), 26.5 (C5), 25.7 (C3'), 14.0 (C4').

Anal. Calcd for C$_{21}$H$_{26}$BNO: C, 79.01; H, 8.21; N, 4.39.

Found: C, 78.58; H, 8.37; N, 4.37.

EXAMPLE 26

Preparation of (S)-Tetrahydro-1,3,3-triphenyl-1H,3H-pyrrolo-[1,2-c][1,3,2]oxazaborole A solution of the free base product of Example 1, Step B (10.3 g, 40.7 mmol) and triphenylboroxine (4.25 g, 13.6 mmol) in toluene (100 mL) was aged 0.5 hour at 20°-25° C., then heated at reflux for 16 hours using a Dean-Stark trap for water removal. The solution was concentrated (1 atm) to a volume of 47 mL. The suitability of the catalyst was determined by both capillary GC: (DB-1, 160° C. for 3 minute, then 10° C./minute to 300° C.) <0.1% benzophenone (2.6 minute), <1% starting material (7.5 minute), <1% triphenylboroxine (10.8 minute), >98% oxazaborolidine product (14.2 minute), and $^1$H NMR: (CDCl$_3$) no starting material δ4.25 (t). Based on the final volume of 47 mL, the concentration of oxazaborolidine product was calculated to be 0.87M. The toluene solution, stored under an atmosphere of N$_2$ protected from moisture, was used "as is" as a catalyst for the enantioselective reduction of ketones with borane.

For analysis, a portion of the toluene solution (5.00 mL) was concentrated in vacuo (50° C., 0.001 mBar) to afford 1.48 g of the product as a colorless glass: IR (CCl$_4$) 3060, 3020, 2960, 2870, 1595, 1445, 1300, 1000 cm$^{-1}$; $^1$H NMR (0.2M in CDCl$_3$) δ8.05-7.95 (m, 2H, Ar-H), 7.70-7.60 (m, 2H, Ar-H), 7.55-7.15 (m, 11H, Ar-H), 4.65 (dd, J=5.5, 9.7 Hz, 1C3a-H), 3.70-3.55 (m, 1H, C6-H), 3.45-3.30 (m, 1H, C6-H), 2.05-1.75 (m, 3H, C4-H, C5-H$_2$), 1.05-0.90 (m, 1H, C4-H); $^{11}$B NMR (CDCl$_3$) δ30.8; $^{13}$C NMR (0.2M in CDCl$_3$) δ147.4, 143.8 (C1'', C1'''), 134.6 (C2', C6'), 130.3 (C4'), 128.2, 127.77 (C3'', C3''', C5'', C5'''), 127.85 (C3', C5'), 127.2, 126.7 (C4'', C4'''), 126.41, 126.35 (C2'', C2''', C6'', C6'''), 87.7 (C3), 74.4 (C3a), 43.8 (C6), 30.0 (C4), 27.6 (C5).

Anal. Calcd for C$_{23}$H$_{22}$BNO: C, 81.43; H, 6.54; N, 4.13.

Found: C, 81.35; H, 6.56; N, 4.12.

Employing the procedure substantially as described in Example 26, but substituting for the triphenylboroxine used therein, comparable amounts of triarylboroxines described in Table III, there were produced the B-aryl oxazaborolidines also described in Table III:

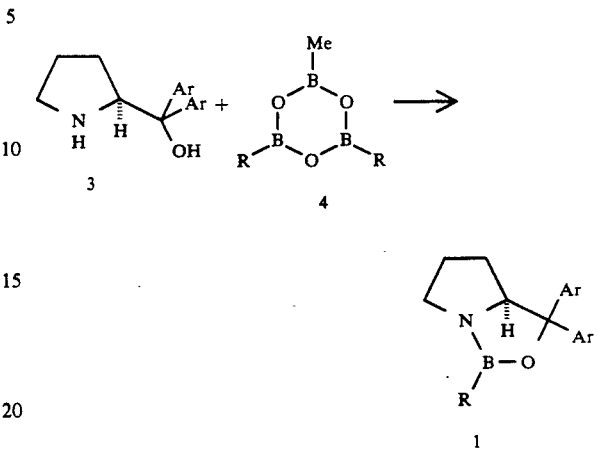

TABLE III

| Example | R | Purity (%) |
|---|---|---|
| 27 | 4-F—C$_6$H$_4$— | 98 |
| 28 | 4-Cl—C$_6$H$_4$— | 97 |
| 29 | 4-CH$_3$—C$_6$H$_4$— | 99 |
| 30 | 4-CF$_3$—C$_6$H$_4$— | 97 |
| 31 | 4-CH$_3$O—C$_6$H$_4$— | 97 |
| 32 | 2,4,6-(CH$_3$)$_3$—C$_6$H$_2$— | 97 |

EXAMPLE 33

Preparation of (S)-Tetrahydro-1-methyl-3,3-diphenyl-1H,3H-pyrrolo[1,2-c][1,3,2]oxazaborole-borane complex To a mechanically stirred solution of the oxazaborolidine decribed in Example 13 (1.28M in toluene) (20.0 mL, 25.6 mmol) at 20° C. was added borane-dimethyl sulfide (10M, 5.0 mL, 50 mmol). The solution was stirred at 20° C. for 12 hours with a nitrogen sweep to remove dimethyl sulfide. The thick white mixture was filtered, and the product cake washed with dry toluene (10 mL). The product was dried in vacuo (20° C., 0.01 mBar) to afford 6.04 g (81% yield) of a white crystalline solid. m.p. 122°-130° C. (dec). $^1$H NMR (CDCl$_3$) δ7.6 (m, 2H, Ar-H), 7.15-7.40 (m, 8H, Ar-H), 4.65 (t, J=7.9 Hz, 1H, C3a-H), 3.4 (m, 1H, C6-H), 3.2 (m, 1H, C6-H), 1.9 (m, 2H, C5-H$_2$), 1.7 (m, 1H, C4-H), 1.3 (m, 1H, C4-H), 2.1-0.8 (very br, 3H, BH$_3$), 0.78 (s, 3H, B-CH$_3$). $^{13}$C NMR (CDCl$_3$) δ144.6, 143.5 (C1', C1''), 128.3, 128.2 (C3', C5', C3'', C5''), 127.4, 127.1 (C4', C4''), 125.4, 125.0 (C2', C6', C2'', C6''), 90.6 (C3), 76.2 (C3a), 57.7 (C6), 31.4 (C4), 25.0 (C5).

Anal. Calcd for C$_{18}$H$_{23}$B$_2$NO: C, 74.29; H, 7.97; N, 4.81.

Found: C, 74.34; H, 8.00; N, 4.69.

The following reaction scheme is described in Example 34, which illustrates the utility of the oxazaborolidine catalysts, particularly in Step E describing the reduction of 9 to 10.

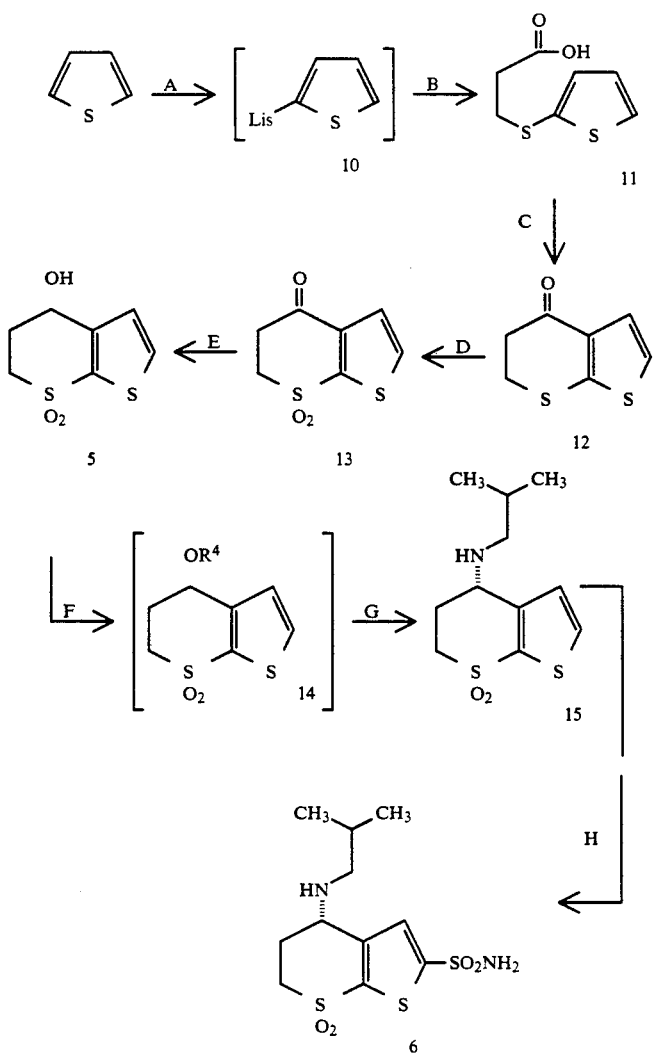

EXAMPLE 34

S-(+)-5,6-Dihydro-4-(2-methylpropyl)amino-4H-thieno[2,3-b]-thiopyran-2-sulfonamide-7,7-dioxide

Steps A and B: Preparation of 3-(2-thienylthio)propanoic acid (11)

In a 2-L, three-neck round-bottom flask fitted with a thermometer, nitrogen inlet, mechanical stirrer and addition funnel was placed thiophene (64 mL, 799 mmol; Caution: stench) and sieve dried THF (400 mL, residual water $\leq 120$ μg/mL). The solution was cooled to 0°–5° C. and 1.6M n-butyllithium (470 mL, 751 mmol) was added at such a rate as to maintain the temperature at <20° C. The reaction was stirred for 1 hour are 0°–5° C., and was used immediately in the next sequence. To the cooled reaction mixture (0°–5° C.) was added sulfur (24 g, 750 mmol) portionwise while maintaining the temperature at <20° C. The reaction was stirred for an additional 2.0 hours at 0°–5° C. after which nitrogen-purged water (300 mL) was added at such a rate as to maintain the temperature at <18° C. The addition of sulfur was highly exothermic. (Note: the 2-mercaptothiophene and its anion (6) can air-oxidize to the corresponding disulfide. Therefore, solutions of 10 must be deoxygenated and stored under a nitrogen atmosphere). Solids may form initially upon addition of water to the solution of 10 but eventually dissolve. The solution of 10 was titrated for total base. The yield of thiophene to 10 based on titration was 98%.

In a 1-L, three-neck, round-bottom flask fitted with an addition funnel, thermometer, nitrogen sweep and mechanical overhead stirrer was prepared a solution of potassium carbonate (46.5 g, 337 mmol) in nitrogen-purged water (85 mL). To this solution was added solid 3-bromopropionic acid (116 g, 736 mmol) at such a rate as to control foaming ($CO_2$ evolution). The mixture was stirred until a clear solution was obtained. The temperature increased from 23° C. to 50° C. during the dissolution of potassium carbonate. (Caution: foaming occurs during the addition). The solution of 10 was cooled to 10° C. and the aqueous solution of potassium 3-bromopropionate was added at such a rate as to maintain the temperature at 0°–5° C. The reaction was stirred for 24 hours at ambient temperature. The layers were separated and the aqueous layer was washed twice with toluene (100 mL portions) to remove neutral organic impurities. The aqueous layer was then cooled to 10° C. and stirred with toluene (300 mL) as aqueous HCl (125 mL, 6N) was added, maintaining the temperature at <14° C. (pH <1). The organic layer was separated and the aqueous layer extracted with additional toluene (300 mL). The organic layers were combined and dried azeotropically under vacuum to a volume of 500 mL and residual water content of <2.5 mg/mL. The solution was stored at 0°-5° C. overnight. A small amount of the carboxylic acid was isolated and characterized as its tert-butylammonium salt: m.p. 110°-112° C. IR (CHCl$_3$): 3400-2300 br s (OH), 2980 m, 2630 m, 2200 w, 1635 m, 1580 br s (C=O), 1480 w, 1390 s, 1300 m, 1270 m, 990 w, 930 w, 850 w. $^1$H NMR: δ8.36 (br s, NH$_3^+$), 7.29 (d, J=5.4, H$_{5'}$), 7.07 (d, J=3.5, H$_{3'}$), 6.93 (dd, J=5.4, 3.5, H$_{4'}$), 2.99 (m, C$_2$H$_2$), 2.43 (m, C$_3$H$_2$), 1.27 (s, C(CH$_3$)$_3$). $^{13}$C NMR: δ177.9 (C$_1$), 134.5 (C$_{2'}$), 133.5, 129.0, 127.4 (C$_{3'}$, C$_{4'}$, C$_{5'}$), 50.6 (C(CH$_3$)$_3$), 38.4, 35.6 (C$_2$, C$_3$), 27.8 (C(CH$_3$)$_3$).

Anal. Calcd for C$_{11}$H$_{19}$NO$_2$S$_2$: C, 50.54; H, 7.33; N, 5.36.
Found: C, 50.53; H, 7.12; N, 5.27.

Step C: Preparation of
5,6-Dihydro-4H-thieno[2,3-b]-thiopyran-4-one (12)

In a 2-L three-neck round-bottom flask fitted with an overhead mechanical stirrer, thermometer, addition funnel, reflux condenser, and nitrogen bubbler vented through an acid-vapor scrubber was placed the toluene solution of 11 (130.7 g, 695 mmol). The reaction mixture was brought to an initial temperature of 20° C. and trifluoroacetic anhydride (161 g, 765 mmol) was added over 5 minutes to the stirred solution of 11. The reaction was then heated to 35°-38° C. and stirred for about 1.5 hours. The reaction was then slowly added to water (500 mL) maintaining the temperature at <25° C. A pH probe was placed in the vessel and the mixture was titrated to pH 7.0 with 50% sodium hydroxide (123 g, 1.53 mole). The layers were separated and the aqueous phase was extracted once with toluene (200 mL). The combined organic extracts were then concentrated under vacuum (43 mbar) to a volume of 200 mL and then diluted to 1.2 L with ethyl acetate for the next step (oxidation). A small sample was chromatographed to obtain the following data: R$_f$=0.29 (85:15 hexane:ethyl acetate). m.p. 61°-62° C. IR (CHCl$_3$): 3120 w, 3090 m, 3010 m, 2930 w, 1660 s (C=O), 1500 m, 1390 s, 1315 w, 1280 w, 1265 m, 1190 w, 1035 w, 890 w. $^1$H NMR: δ7.42 (d, J=5.4, H$_2$); 6.98 (d, J=5.4, H$_3$); 3.33 (m, C$_5$H$_2$); 2.82 (m, C$_6$H$_2$). $^{13}$C NMR: δ188.9 (C$_4$), 150.9, 135.0 (C$_{3a}$, C$_{7a}$), 126.1, 121.8 (C$_2$, C$_3$), 38.1 (C$_6$), 30.0 (C$_5$).

Anal Calcd for C$_7$H$_6$OS$_2$: C, 49.39; H, 3.55; S, 37.66.
Found: C, 49.56; H, 3.58; S, 37.68.

Step D: Preparation of
5,6-Dihydro-4H-thieno[2,3-b]-thiopyran-4-one-7,7-dioxide (13)

The ethyl acetate/toluene solution of ketone 12 (118 g, 765 mmol in 1.2 L of 5:1 v:v EtOAc/toluene) was charged to a 5-L three-neck round-bottom flask equipped with an overhead mechanical stirrer, 250-mL pressure-equalizing dropping funnel, and thermocouple temperature probe. The mixture was stirred and water (35 mL) was added to saturate the organic phase. A solution of sodium tungstate dihydrate (11.7 g, 77 mmol) dissolved in water (35 mL) was then added (Caution: there is an induction period of several minutes before an exotherm). The mixture was heated to 35° C. and hydrogen peroxide (30%, 250 mL, 2.43 mole) was added over 45 minutes. The temperature of the reaction was allowed to rise to 55°-58° C. and was maintained there, initially with cooling and subsequently with heating. The reaction temperature was maintained at 55°-58° C. until judged complete by HPLC: column A, (1 mL/minute, 50:50 0.01M H$_3$PO$_4$ in H$_2$O:CH$_3$CN, 240 nm) R$_t$ (12) 6.18 minutes, (13) 4.07 minutes. On completion the mixture was cooled to 0°-5° C. and excess hydrogen peroxide was decomposed by the slow addition of aqueous sodium sulfite (205 g, 1.63 mole dissolved in 700 mL water). The temperature of the reaction mixture was maintained at <20° C. When the reaction mixture tested negative for peroxide to acidified starch-iodide paper, the layers were separated. The upper organic layer was concentrated under vacuum at 45° C. bath temperature to a volume of 400 mL. Hexanes (400 mL) were then added over about 10 minutes and the batch was aged for one hour. The product was filtered, washed with hexanes, and dried under vacuum at 60° C. with a nitrogen sweep to constant weight. The yield of crude ketosulfone 13 was 113 g (76% from 3-bromopropionic acid). Crude ketosulfone was then recrystallized from methanol using the following procedure. Crude ketosulfone (113 g) was dissolved in anhydrous methanol (3 L) at 55°-60° C. The solution was cooled to 40° C. and 10 g of Calgon ADP carbon was added. The mixture was aged at 40° C. for a minimum of 4 hours. The batch was then filtered warm at 40° C. through a well-washed pad of SuperCel. The filter cake was washed with methanol (2×500 mL) at 40° C. and the filtrates were combined. The batch was then concentrated under vacuum to a volume of 500 mL and aged at 0°-5° C. for 4 hours. Crystallization ensued during concentration. The batch was filtered, washed with 75 mL cold methanol, sucked dry under nitrogen, and dried under vacuum (100 Torr) at 80° C. with a nitrogen sweep for 12 hours. The recovery yield was 100 g (89%) assayed δ99.6 wt % by HPLC against an external stand ard. R$_f$ =0.30 (dichloromethane). m.p. 121°-121.5° C. IR (CHCl$_3$): 3120 w, 3100 w, 3020 m, 1690 s (C=O), 1500 w, 1410 m, 1390 m, 1330 s (SO$_2$), 1310 m, 1285 m, 1260 m, 1190 s, 1155 s (SO$_2$), 1130 m, 1090 m, 860 s, 820 w. $^1$H NMR: δ7.60 (d, J=5.1, H$_2$); 7.50 (d, J=5.1, H$_3$); 3.76 (m, C$_5$H$_2$); 3.36 (m, C$_6$H$_2$). $^{13}$C NMR: δ186.3 (C$_4$), 147.2 (C$_{3a}$), 139.3 (C$_{7a}$), 130.2 (C$_2$), 126.3 (C$_3$), 52.8 (C$_6$), 37.0 (C$_5$). MS (EI, 70 eV): 202 (M$^+$, 35), 174 (38), 138 (15), 110 (100), 84 (30), 82 (25).

Anal. Calcd for C$_7$H$_6$O$_3$S$_2$: C, 41.57; H, 2.99; S, 31.70.
Found: C, 41.49; H, 3.02; S, 31.60.

Step E: Preparation of
R-(+)-5,6-Dihydro-4H-thieno[2,3-b]-thiopyran-4-ol-7,7-dioxide (5)

Ketosulfone 13 (50.0 g, 0.247 moles) was dissolved in tetrahydrofuran (700 mL) over 4 Å molecular sieves (20 g) and occasionally swirled until the residual water content was <40 μg/mL (about 2 hours). A 2-L three-neck round bottom flask fitted with a mechanical stirrer, nitrogen inlet tube, 500-mL addition funnel and teflon coated thermocouple probe, was charged with 13 (decanted from the sieves). To the solution was added oxazaborolidine catalyst (R=CH$_3$, Ar=C$_6$H$_5$) (14.4 mL of a 0.86M solution in toluene). The resulting solution was cooled to −15° C. In a separate vessel boranedimethyl sulfide (17.3 mL) was dissolved in dry tetrahydrofuran (297 mL; residual water <40 μg/mL). The borane-dimethyl sulfide solution was placed in the addition funnel and added to the ketosulfone/catalyst solution at a rate to maintain the internal temperature at −15° C. (about 30 minutes). After all of the borane was added, the reaction was aged for 30 minutes. An easily stirred precipitate usually forms during the age. The reaction was quenched by the cautious addition of 10 mL of methanol (Caution: there was a significant induction period (1-2 minutes) before hydrogen was evolved after the initial methanol was added) maintaining the temperature at −10° C. After hydrogen evolution subsides, methanol (365 mL) was added. The reaction becomes homogeneous during the quench. After complete addition of methanol, the reaction mixture was warmed to 20° C. and stirred for 12 hours. The resulting solution was concentrated at atmospheric pressure to about 125 mL. Methanol (375 mL) was added and the resulting solution was concentrated at atmospheric pressure to 125 mL to remove any remaining volatile boron species.

Amberlyst 15 resin (56 g, 100 mL dry) was suspended in methanol (100 mL). (Caution: the slurry exotherms to about 40° C. without external cooling and expands on wetting to about 1.5 times its initial volume). The slurry was poured into a 2.5×30 cm column and eluted with 1 L of ammonium hydroxide (15M) in methanol (6 vol %, about 1M) until the eluate was basic (pH about 11 when diluted 1:1 with water). The initial brown eluate was discarded. The column was eluted with methanol (about 500 mL) until the eluate was neutral. The methanol solution of (R)-hydroxy sulfone (about 50 g) and (S)-diphenylprolinol (3.13 g) was filtered through a pad of SuperCel. The cake was washed with methanol (2×50 mL) and the combined filtrates brought to a volume of 500 mL (10 mL/g) with methanol. The filtered methanol solution was eluted through the column containing Amberlyst 15 ($NH_4^+$) at 3.8 mL/minute collecting 38 mL fractions. The column was rinsed with methanol (380 mL) to remove all of the product hydroxysulfone. The column was then eluted with 94:6 (v/v) methanol/15M aqueous ammonia (400 mL) to elute diphenylprolinol. Fractions 3-21 containing (R)-hydroxysulfone (95:5 R:S, 49 g (98%), contaminated with less than 0.4% diphenylprolinol) were combined and concentrated (recrystallization of this material from hexane/ethyl acetate only serves to lower enantiomeric purity). Addition of tetrahydrofuran (500 mL) followed by concentration to 250 mL was repeated twice. Tetrahydrofuran was added to generate a solution of 5 in a total volume of 500 mL for use in the next reaction. Fractions 29-33 containing (S)-diphenylprolinol (<1:99 R:S, 3.0 g) were combined and concentrated to afford a crystalline solid. The progress of the column can be monitored by HPLC: column A (1 mL/minute, 60:40 0.01M $KH_2PO_4$ in $H_2O:CH_3CN$) $R_t$ (9) 4.78 minutes (240 nm), (10) 3.30 minutes (240 nm), (diphenylprolinol) 5.60 minutes (210 nm). A small sample was chromatographed to obtain characterization data: $R_f$=0.07 (60:40 hexane:ethyl acetate). $[\alpha]_{589}^{21}$ = +16.4° (c 0.210, MeOH). m.p. 89°-90° C. IR ($CHCl_3$): 3600 w (OH), 3550-3400 br w (OH), 3110 w, 3010 m, 2940 w, 1520 w, 1400 m, 1305 s ($SO_2$), 1285 s, 1180 w, 1145 s ($SO_2$), 1125 s, 1100 w, 1160 m, 1140 m, 970 w, 915 w, 890 w, 845 w, 825 m. $^1H$ NMR: δ7.59 (d, J=5.1, $H_2$), 7.12 (d, J=5.1, $H_3$), 4.91 (ddd, J=10.0, 5.9, 1.5, $H_4$), 3.62 (m, $H_6$), 3.31 (m, $H_6$), 2.75 (m, $H_5$), 2.55 (m, $H_5$, OH). $^{13}$NMR: δ144.9 ($C_{3a}$), 135.9 ($C_{7a}$), 130.5 ($C_2$), 127.0 ($C_3$), 63.5 ($C_4$), 49.1 ($C_6$), 31.0 ($C_5$).

Anal. Calcd for $C_7H_8O_3S_2$: C, 41.16; H, 3.95; S, 31.39.
Found: C, 41.23; H, 3.93; S, 31.24.

Chiral Assay: To alcohol 5 (20 mg) in dry dichloromethane (2 mL) was added N,N-dimethylaminopyridine (12 mg, 1.0 equiv), triethylamine (14 mL, 10 mg, 3.0 equiv) and (R)-(+)-α-methoxy-α-(trifluoromethyl)phenylacetic acid chloride (Mosher acid chloride, 27 mg, 21 mL, 1.1 equiv, see General of Experimental Section). The mixture was stirred for 1-5 hours, as judged by TLC (EM Si-60, 6:4 hexane/EtOAc, $R_f$ alcohol 5=0.10, $R_f$ ester=0.60). The reaction mixture was diluted with hexane (8 mL) and centrifuged (5 minutes). The resulting clear yellow solution was eluted through a Baker Silica SPE (1 g) column (previously washed with 5 mL of hexane). The initial eluate was discarded, and 6:4 hexane/EtOAc (10 mL) was eluted and collected. The latter eluate was then analyzed by capillary GC on column A: (15 psi, 200° C., isothermal) $R_t$ ((R,R)-Mosher ester (major), 10.0 minutes; (R,S)-Mosher ester (minor), 10.4 minutes. Enantiomeric purity: >95:5.

Steps F and G: Preparation of
S-5,6-Dihydro-N-(2-methylpropyl)-4H-thieno[2,3-b]-thiopyran-4-amine-7,7-dioxide (15)

A 3-L three-neck flask fitted with a mechanical stirrer, nitrogen inlet tube, 500-mL addition funnel and teflon coated thermocouple probe was charged with a slurry of sodium acetylide in xylene/light mineral oil (Aldrich, 71.9 g, 0.270 mol of an 18% slurry) and was well mixed with 400 mL of tetrahydrofuran. Hydroxysulfone 5 (50.0 g, 0.245 moles) dissolved in dry tetrahydrofuran (500 mL, see above; residual water content should be <100 μg/mL) and placed in the addition funnel. The solution was cooled to 15° C. and the solution of 10 was added to the sodium acetylide over about 5 minutes. (Caution: sodium acetylide is moisture sensitive and generates acetylene upon addition of water). The resulting suspension was stirred at 20° C. for 2 hours. During the age, the fine slurry of sodium acetylide was converted to the easily stirred, coarse, crystalline sodium salt of the hydroxysulfone. (The deprotonation can be monitored by removing a 1 mL aliquot and adding it to excess toluenesulfonyl chloride (45 mg, 0.24 mmol) in 1 mL of tetrahydrofuran and monitoring by TLC: 60:40 hexane:ethyl acetate; $R_f$ hydroxysulfone 10, 0.07; tosylate 14, 0.37). The resulting slurry was cooled to −15° C. Toluenesulfonyl chloride (51.3 g, 0.269 mol) was dissolved in 250 mL of tetrahydrofuran and placed in the addition funnel. The toluenesulfonyl chloride/tetrahydrofuran solution was added to the sodium salt at a rate to maintain the internal temperature below −10° C. (about 10 minutes). The resulting mixture was aged at −10° C. for 2 hours. The tosylation can be followed by TLC (60:40 hexane:ethyl acetate; $R_f$: tosylate 11, 0.37; hydroxysulfone 10, 0.07). The sodium salt of the hydroxysulfone dissolved during the age and the reaction usually turned dark green. (Note: tosylate 11 should not be isolated since it readily hydrolyzes to racemic 10 in water). Dry (residual water <100 μg/mL) isobutylamine (250 g, 340 mL, 3.43 mol) was added over 5 minutes. The resulting mixture was warmed to 20° C. and aged for 14 hours. (This reaction was monitored by TLC: 60:40 hexane:ethyl acetate; $R_f$: tosylate 11, 0.37; amine 15, 0.25). The resulting mixture was cooled to −15° C. and aqueous hydrochloric acod (1.54 L, 2N) was added at a rate to maintain the internal temperature at or below 5° C. (about 30 minutes). The resulting pH was about 2.5. The solution was concentrated to about 1.6 L to remove most (90%) of the tetrahydrofuran and extracted with isopropyl acetate (2×600 mL). The aqueous phase was cooled to 0° C. and sodium hydroxide (120 mL, 5N) was added at a rate to maintain the internal temperature below 5° C. (about 5 minutes). The resulting pH was about 10 and the reaction mixture became cloudy upon addition of sodium hydroxide. The resulting mixture was extracted twice with isopropyl acetate (600 mL). The organic layers were combined and concentrated to about 120 mL. Isopropanol (600 mL) was added and the mixture was concentrated to 100 mL. A second flush was performed to remove the isopropyl acetate. (Solubility of amine 15 in isopropanol: 2.5 mg/mL at −20° C.; 7.3 mg/mL at 0° C.; 28.3 mg/mL at 20° C.; 151 mg/mL at 45° C.). Isopropanol was added to bring the volume to about 1 L and the resulting solution was warmed to 55°-60° C. and Calgon ADP (5 g) decolorizing carbon was added. The mixture was stirred at 50° C. for 4 hours. The resulting mixture was filtered (at 50° C.) through pre-washed SuperCel. The filtered solution was concentrated to 0.86 L (14 mL/g amine) and allowed to cool slowly to room temperature. The resulting suspension was cooled to 0° C. and aged for 2 hours. The suspension was filtered, washed twice with 150 mL of 0° C. isopropanol and dried in vacuo at 45° C. for 12 hours to yield 47 g (73%) of amine 15 (R=2-methylpropyl) as off white crystals.

Data for 15: $R_f$=0.25 (60:40 hexane:ethyl acetate). $[\alpha]_{589}^{22}$ = −8.68° (c 0.316, MeOH). m.p. 86°-86.5° C. IR (CHCl$_3$): 3110 w, 3010 m, 2960 m, 2950 sh, 2900 w, 2870 w, 2830 w, 1520 w, 1460 m, 1400 m, 1365 w, 1305 s (SO$_2$), 1280 m, 1140 s (SO$_2$), 1090 m, 1055 w, 890 w, 850 w, 830 w. $^1$H NMR: δ7.53 (d, J=5.0, H$_2$), 7.08 (d, J=5.0, H$_3$), 3.91 (dd, J=6.3, 4.1, H$_4$), 3.68 (ddd. J=13.6, 9.8, 2.8, H$_6$), 3.27 (ddd, J=9.3, 8.8, 2.6, H$_6$), 2.55 (m, C$_5$H$_2$, C$_1'$H$_2$), 1.68 (nine lines, J=6.6), 0.92 (d, K=6.8). $^{13}$C NMR: δ146.0 (C$_{3a}$), 135.6 (C$_{7a}$), 129.7 (C$_2$), 127.1 (C$_3$), 55.0 (C$_{1'}$), 52.6 (C$_4$), 49.6 (C$_6$), 28.8 (C$_{2'}$), 27.8 (C$_5$), 20.6, 20.5 (2×CH$_3$).

Anal. Calcd for C$_{11}$H$_{17}$NO$_2$S$_2$: C, 50.94; H, 6.61; N, 5.40; S, 24.72.

Found: C, 51.00; H, 6.64; N, 5.30; S, 24.50.

Chiral Assay: To amine 15 (10 mg) in dry ethyl acetate (1 mL) was added trifluoroacetic anhydride (20 mL). The mixture was stirred for 1-5 minutes, as judged by TLC (EM Si-60, 6:4 hexane/EtOAc, $R_f$: amine 15, 0.30; amide, 0.50). The reaction mixture was concentrated to dryness and then diluted with tetrahydrofuran (2 mL). The resulting clear yellow solution was eluted through a Baker quaternary amine SPE (1 g) column (previously washed with 5 mL of isopropanol). The eluate was collected, and 88:11:1 hexane/tetrahydrofuran/isopropanol (20 mL) was eluted and collected. The eluate was then analyzed by normal phase HPLC (250 nm): column B (2.0 mL/minute, 88:11:1 hexane:tetrahydrofuran:isopropanol, isocratic): $R_f$: (R)-TFA-12 10.65 minutes; (S)-TFA-12 12.82 minutes. Enantiomeric purity >99:1.

Step H: Preparation of S-(+)-5,6-Dihydro-4-(2-methylpropyl)amino-4H-thieno[2,3-b]thiopyran-2-sulfonamide-7,7-dioxide monohydrochloride hemihydrate (16)

A 1-L round-bottom flask fitted with a mechanical stirrer, nitrogen inlet and septum was charged with fuming sulfuric acid (12-20% SO$_3$ in H$_2$SO$_4$, 125 mL). (Caution: fuming sulfuric acid (oleum) is extremely corrosive). The solution was cooled to −15° C. and amine 15 (R=2-methylpropyl) (25 g, 96.4 mmol) was added portionwise at a rate to maintain the temperature <0° C. (Caution: the addition is exothermic). After stirring the resultant solution for 2 hours at 5°-8° C., thionyl chloride (375 mL, 611 g, 5.14 mol) was added and the mixture was refluxed for 3 hours. The thionyl chloride was removed by distillation and the resulting oil was cooled to 0° C. A 5-L round-bottom flask fitted with a mechanical stirrer, 250-mL pressure equalizing addition funnel (with a teflon tube attached to the bottom that reached below the surface of the contained liquid) and nitrogen inlet was charged with concentrated aqueous ammonia (800 mL) and tetrahydrofuran (800 mL) and cooled to −15° C. The addition funnel was charged with the sulfuric acid solution of the sulfonyl chloride. The sulfuric acid solution was slowly added (subsurface) to the ammonia mixture at a rate to maintain the temperature below 0° C. (about 1 hour). (Caution: addition of strong acid to strong base is exothermic and spattering may occur). After complete addition, the resulting mixture was stirred at 0° C. for 30 minutes. The resulting pH was 10. The resulting suspension was filtered and the filter cake washed twice with tetrahydrofuran (600 mL). The filtrate was concentrated to remove tetrahydrofuran and extracted twice with ethyl acetate (600 mL). The organic layers were combined, concentrated to 375 mL and stirred well as concentrated hydrochloric acid (12 mL, 145 mmol) was slowly added. The mixture was concentrated under vacuum at 45° C. (bath temperature) to necessary, until a solution with a water content of <0.1 mg/mL was attained at a volume of about 350 mL. The crystallized mixture was allowed to cool and stirred at ambient temperature overnight. The slurry was filtered and washed with two bed volumes of ethyl acetate. The white solid was dried under vacuum at 45° C. to afford 26 g of 6 (R=2-methylpropyl) hydrochloride. The salt could be recrystallized from water as follows: 6 (R=2-methylpropyl) hydrochloride (25 g, 73 mmol) was dissolved in water (50 mL) at 90° C. The mixture was well stirred and activated carbon (Darco KB, 2.5 g) was added to the hot mixture. After stirring for 2 hours, the mixture was filtered hot (85°-90° C.) through a washed bed of SuperCel and the filter cake washed with 10 mL of boiling water. The combined filtrate and wash was allowed to slowly cool to 40°-50° C. and held at 40°-50° C. until crystallization occurred. After stirring for 1 hour at 55° C. after crystallization occurred, the mixture was cooled to 3° C. and aged for 1 hour. The resulting mixture was filtered and the filter cake washed with cold water (10 mL). The product was dried under vacuum at 45° C. with a nitrogen sweep to afford 21 g (71%) of 6 (R=2-methylpropyl) hydrochloride. This sequence can be monitored by HPLC: column A, (1 mL/minute, 55:45 0.01M K$_2$HPO$_4$ in H$_2$O:CH$_3$CN, 240 nm) $R_f$: sulfonic acid, 2.37 minutes; (13), 6.34 minutes; (12), 8.54 minutes; tricycle byproduct, 10.17 minutes. $[\alpha]_{589}^{25}$ = +49 (c 0.50, MeOH). m.p. 222° C. (dec). IR (KBr): 3350 w (NH), 2950 s, 2800-2300 w (NH$_2$+), 1620 w, 1540 m, 1466 w, 1420 w, 1400 w, 1350 s (SO$_2$), 1340 s (SO$_2$), 1300 s (SO$_2$), 1160 s (SO$_2$), 1145 s (SO$_2$), 1050 m, 1020 m, 910 w, 880 m, 740 m, 700 w. $^1$H NMR (DMSO-d$_6$): δ9.82 (br s, C$_4$NH$_2$+), 8.20 (s, SO$_2$NH$_2$), 8.16 (s, C$_3$H), 4.80 (br s, C$_4$H), 3.94 (m, C$_6$H$_2$), 3.83 (s, H$_2$O), 2.82 (m, C$_5$H$_2$, C$_1'$H$_2$), 2.15 (septet, J=6.6, C$_2'$H), 0.98 (d, J=6.6, CH$_3$), 0.96 (d, J=6.6, CH$_3$). $^{13}$C NMR (DMSO-d$_6$): δ149.4 (C$_2$), 141.8 (C$_{7a}$), 137.5 (C$_{3a}$), 129.8 (C$_3$), 51.2 (C$_6$), 50.9 (C$_4$), 48.3 (C$_{1'}$), 25.5 (C$_{2'}$), 23.7 (C$_5$), 20.3, 20.0 (2×CH$_3$). HRMS (free base, EI, 90 eV) Calcd for C$_{11}$H$_{18}$N$_2$O$_4$S$_2$: 338.0429. Found: 338.0430.

Anal. Calcd for C$_{11}$H$_{19}$ClN$_2$O$_4$S$_3$0.5 H$_2$O: C, 34.41; H, 5.25; N, 7.30; S, 25.05; Cl, 9.23.

Found: C, 34.55; H, 5.20; N, 7.21; S, 24.89; Cl, 9.50.

Employing procedures substantially as described in Example 34 Step E but substituting for the ketone 13 substrate and the oxazaborolidine used therein, the ketone and oxazaborolidine described in Table IV, there were produced the corresponding secondary alcohols in the enantiomeric ratios shown therein.

mL, 4.0 mmol) in dry THF (6.8 mL) was added at a rate to maintain the internal temperature at −15° C. The solution was stirred at −15° C. for 1 hour. The product was isolated by the method decribed in Example 34 Step E. The enantiomeric ratio of the purified product was 99:1.

TABLE IV

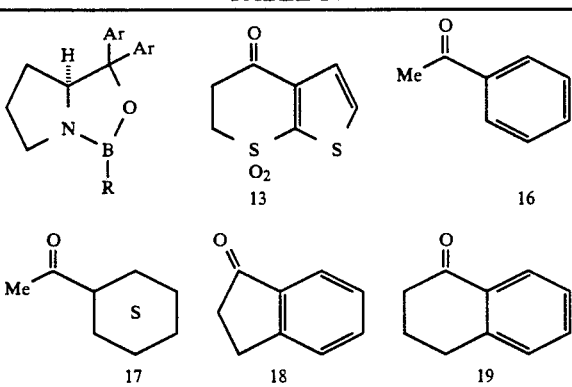

| R | Ar | 9 | 14 | 15 | 16 | 17 |
|---|---|---|---|---|---|---|
| CH₃— | C₆H₅— | 98:2 | 99:1 | 82:18 | 98:2 | 97:3 |
| CH₃— | 4-F—C₆H₄— | 97:3 | 84:16 | 85:15 | 97:3 | 94:6 |
| CH₃— | 4-Cl—C₆H₄— | 97:3 | 90:10 | 82:18 | 96:4 | 94:6 |
| CH₃— | 4-CH₃—C₆H₄— | 96:4 | 86:14 | 83:17 | 95:5 | 95:5 |
| CH₃— | 4-CF₃—C₆H₄— | 98:2 | 95:5 | 88:12 | 96:4 | 96:4 |
| CH₃— | 4-t-Bu—C₆H₄— | 95:5 | 93:7 | 84:16 | 98:2 | 91:9 |
| CH₃— | 4-CH₃O—C₆H₄— | 97:3 | 95:5 | 84:16 | 95:5 | 97:3 |
| CH₃— | 3-Cl—C₆H₄— | 96:4 | 93:7 | 86:14 | 96:4 | 98:2 |
| CH₃— | 3,5-Cl₂—C₆H₃— | 96:4 | 90:10 | 80:20 | 92:8 | 95:5 |
| CH₃— | 3,5-(CH₃)₂—C₆H₃— | 96:4 | 97:3 | 86:14 | 96:4 | 97:3 |
| CH₃— | 2-naphthyl | 96:4 | 89:11 | 82:18 | 96:4 | 96:4 |
| n-C₄H₉— | C₆H₅— | 93:7 | 96:4 | 88:12 | 95:5 | 98:2 |
| C₆H₅— | C₆H₅— | 98:2 | 86:14 | 77:23 | 91:9 | 97:3 |
| 4-F—C₆H₄— | C₆H₅— | 99:1 | 94:6 | 76:24 | 88:12 | 97:3 |
| 4-Cl—C₆H₄— | C₆H₅— | 98:2 | 87:13 | 72:38 | 86:14 | 94:6 |
| 4-CH₃—C₆H₄— | C₆H₅— | 99:1 | 94:6 | 81:19 | 92:8 | 97:3 |
| 4-CH₃O—C₆H₄— | C₆H₅— | 97:3 | 85:15 | 76:24 | 92:8 | 95:5 |

EXAMPLE 35

Preparation of (R)-(+)-5,6-Dihydro-4H-thieno[2,3-b]-thiopyran-4-ol-7,7-dioxide (5)

To a magnetically stirred solution of 5,6-Dihydro-4H-thieno[2,3-b]-thiopyran-4-one-7,7-dioxide (13) (1.00 g, 4.94 mmol) in dry THF (14 mL) was added (S)-diphenylprolinol-borane complex from Example 12 (132 mg, 0.494 mmol). The solution was cooled to −15° C. and a solution of borane-dimethyl sulfide (10M, 0.4 mL, 4.0 mmol) in dry THF (6.8 mL) was added at a rate to maintain the internal temperature at −15° C. The solution was stirred at −15° C. for 1 hour then at 22° C. for 6 hours. The product was isolated by the method decribed in Example 34 Step E. The enantiomeric ratio of the purified product was 95:5.

EXAMPLE 36

Preparation of (R)-(+)-5,6-Dihydro-4H-thieno[2,3-b]-thiopyran-4-ol-7,7-dioxide (5)

To a magnetically stirred solution of 5,6-Dihydro-4H-thieno[2,3-b]-thiopyran-4-one-7,7-dioxide (13) (1.00 g, 4.94 mmol) in dry THF (14 mL) was added (S)-Tetrahydro-1-methyl-3,3-diphenyl-1H,3H-pyrrolo[1,2-c][1,3,2]oxazaborole-borane complex from Example 33 (144 mg, 0.494 mmol). The solution was cooled to −15° C. and a solution of borane-dimethyl sulfide (10M, 0.4

What is claimed is:

1. A compound of structural formula

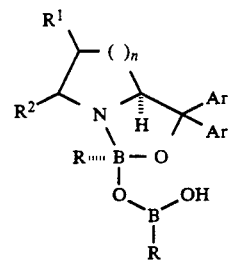

wherein:
n is 1;
R is
1) C₁₋₄alkyl,
2) phenyl,
3) phenyl substituted with one or more of:
   i) halo,
   ii) C₁₋₄alkyl,
   iii) CF₃, or
   iv) C₁₋₄alkoxy,
R¹ and R² independently are hydrogen, C₁₋₃alkyl, or joined together represent with the carbons to which they are attached a benzo group or a double bond;

Ar is
1) 2-naphthyl,
2) phenyl,
3) phenyl substituted in the 3- or 4-position, with one or more of
   i) halo,
   ii) $C_{1-14}$alkyl,
   iii) $CF_3$, or
   iv) $C_{1-4}$alkoxy.

2. The compound of claim 1 wherein n is 1, and $R^1$ and $R^2$ are hydrogen.

3. The compound of claim 2 wherein Ar is phenyl.

4. The compound of claim 3 wherein R is methyl, 4-fluorophenyl or 4-methylphenyl.

5. The compound of structural formula:

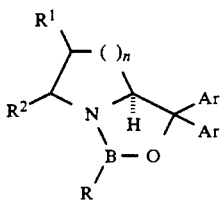

wherein:
n is 1;
R is
1) phenyl,
2) phenyl substituted with one or more of:
   i) halo,
   ii) $C_{1-4}$alkyl,
   iii) $CF_3$, or
   iv) $C_{1-4}$alkoxy.

$R^1$ and $R^2$ independently are hydrogen, $C_{1-3}$alkyl, or joined together form, with the carbons to which they are attached, a benzo group or a double bond;
Ar is
1) 2-naphthyl,
2) phenyl,
3) phenyl substituted in 3- and or 4-position with one or more of:
   i) halo,
   ii) $C_{1-4}$alkyl,
   iii) $CF_3$, or
   iv) $C_{1-4}$alkoxy.

6. The compound of claim 5 wherein n is 1; $R^1$ and $R^2$ are hydrogen, and R is 4-fluorophenyl or 4-methylphenyl.

7. A compound of structural formula

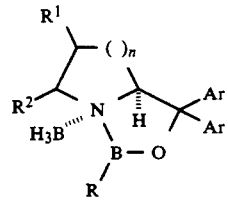

recovered from the reaction mixture wherein
n is 1;
R is
1) $C_{1-4}$alkyl,
2) phenyl,
3) phenyl substituted with one or more of:
   i) halo,
   ii) $C_{1-4}$alkyl,
   iii) $CF_3$, or
   iv) $C_{1-4}$alkoxy, $R^1$ and $R^2$ independently are hydrogen, $C_{1-3}$alkyl, or joined together form, with the carbons to which they are attached, a benzo group or a double bond;
Ar is
1) 2-naphthyl,
2) phenyl,
3) phenyl substituted in 3- and or 4-positioned with one or more of:
   i) halo,
   ii) $C_{1-4}$alkyl,
   iii) $CF_3$, or
   iv) $C_{1-4}$alkoxy.

8. A compound of claim 7 wherein n is 1, and $R^1$ and $R^2$ are hydrogen, and Ar is phenyl.

9. A compound of claim 8 wherein R is methyl, 4-fluorophenyl or 4-methylphenyl.

10. The compound of claim 9 wherein R is methyl.

11. A compound of claim 7 in crystalline form.

* * * * *